United States Patent [19]
Johnson

[11] Patent Number: 5,376,359
[45] Date of Patent: Dec. 27, 1994

[54] METHOD OF STABILIZING AEROSOL FORMULATIONS

[75] Inventor: Keith A. Johnson, Durham, N.C.

[73] Assignee: Glaxo, Inc., Research Triangle Park, N.C.

[21] Appl. No.: 909,596

[22] Filed: Jul. 7, 1992

[51] Int. Cl.$^5$ .......................... A61K 9/14; A61K 47/30
[52] U.S. Cl. ........................................ 424/46; 424/45; 424/489; 514/957; 514/958; 514/970; 514/772.3
[58] Field of Search ................ 424/45, 46, 78.37, 489; 514/957, 958, 970, 772.3, 826, 856–859, 869, 929

[56] References Cited

U.S. PATENT DOCUMENTS

| | | | |
|---|---|---|---|
| 4,347,236 | 8/1982 | Tanskanen | 424/45 |
| 4,352,789 | 10/1982 | Thiel | 424/46 |
| 4,978,389 | 12/1990 | Sato et al. | 528/395 |
| 5,118,494 | 6/1992 | Schultz et al. | 424/45 |
| 5,126,123 | 6/1992 | Johnson | 424/45 |

FOREIGN PATENT DOCUMENTS

| | | |
|---|---|---|
| 91/14422 | 3/1991 | WIPO . |
| 91/11173 | 8/1991 | WIPO . |
| 02/00061 | 9/1992 | WIPO . |

OTHER PUBLICATIONS

Giovanni Pantini, *Montefluos S.p.a.* FOMBLIN HC Cosmetic Formulary.
Giovanni Pantini et al. *Perfluoropolyethers For Cosmetics,* in Drug and Cosmetic Industry (Sep. 1988).

*Primary Examiner*—Edward J. Webman
*Attorney, Agent, or Firm*—Bell, Seltzer, Park & Gibson

[57] ABSTRACT

A method of making a stabilized aerosol drug formulation is disclosed, along with the formulations so produced and metered drug inhalers containing the same. The method comprises combining a solid particulate drug composition with a fluoropolymer in a liquid fluorocarbon aerosol propellant to form a stable suspension. Further stabilization can be achieved by cooling the suspension for a time and to a temperature sufficient to adsorb the fluoropolymer to the solid particulate drug composition in the liquid fluorocarbon aerosol propellant. Preferred propellants for carrying out the invention are 1,1,1,2-tetrafluoroethane, heptafluoropropane, and mixtures thereof, and preferred fluoropolymers for carrying out the invention are fluoropolyethers.

21 Claims, No Drawings

METHOD OF STABILIZING AEROSOL FORMULATIONS

FIELD OF THE INVENTION

This invention relates to methods of stabilizing an aerosol formulation containing solid drug particles, including methods in which a cooling step is employed to further stabilize the formulation.

BACKGROUND OF THE INVENTION

Drugs for treating respiratory and nasal disorders are frequently administered in aerosol formulations through the mouth or nose. See generally P. Byron, *Respiratory Drug Delivery*, CRC Press, Boca Raton, Fla. (1990). One widely used method for dispensing such an aerosol drug formulation involves making a suspension formulation of the drug as a finely divided powder in a liquefied gas known as a propellant. The suspension is stored in a sealed container capable of withstanding the pressure required to maintain the propellant as a liquid. The suspension is dispensed by activation of a dose metering valve affixed to the container.

A metering valve may be designed to consistently release a fixed, predetermined amount of the drug formulation upon each activation. As the suspension is forced from the container through the dose metering valve by the high vapor pressure of the propellant, the propellant rapidly vaporizes, leaving a cloud of very fine particles of the drug formulation. This cloud is usually directed into the body of the patient by a channeling device, e.g., a cylinder-like or cone-like passage, with one of its ends attached to the outlet of the pressurized container, and the other end inserted in the mouth or nose of the patient. Concurrently with the activation of the aerosol dose metering valve, the patient inhales the drug formulation particles into the lungs or nasal cavity. Systems for dispensing drugs in this way are known as "metered dose inhalers (MDI's)." See Byron, supra at 167–207.

Many materials, including drug formulations, have a tendency to aggregate (also referred to as "flocculate" or "clump-up") when stored as fine particles having dimensions of a few microns in a suspension. For an aerosol delivery system to work properly the particle size should generally not exceed about five microns. As the particle size exceeds five microns, it becomes increasing difficult to maintain an efficacious aerosol dose with a predicable dispersion pattern upon activation of the metering valve. Further, the suspension should be uniform, that is, substantially free from large aggregates of the drug particle and be substantially homogenous throughout the container.

To minimize or prevent the problem of aggregation of fine particles, compounds known as surface active agents, or surfactants, are often used to coat the surfaces of the fine particles and assist in wetting the particles with an aerosol propellant. The use of surfactants in this way to maintain substantially uniform suspensions is said to "stabilize" the suspensions.

For several years the chlorofluorocarbons (CFC's) have gained widespread acceptance as the propellants of choice for inhalation drug formulations. However, in the past few years CFC's have been shown to cause depletion of the ozone layer of the atmosphere: a serious environmental problem. Scientists and governmental officials around the world have called for a phase-out of the use of CFC's, and some countries, e.g., Sweden, have banned their use entirely.

In recent years hydrofluorocarbon (HFC) propellants such as 1,1,1,2-tetrafluoroethane (also known as "propellant 134a") and heptafluoropropane (also known as "propellant 227") have been promoted as an environmentally acceptable alternative to CFC propellants. While attractive in many respects, in the area of aerosol pharmaceuticals it has proven particularly difficult to form stablized compositions with such propellants. In light of the need to reduce the use of CFC propellants, there is a continuing need for the development of stabilized aerosol formulations containing HFC propellants.

SUMMARY OF THE INVENTION

Disclosed herein is a method of making a stabilized aerosol drug formulation. The method comprises combining a solid particulate drug composition with a fluoropolymer in a liquid fluorocarbon aerosol propellant to form a liquid suspension, wherein the fluoropolymer is soluble in the liquid fluorocarbon aerosol propellant.

Also disclosed herein is a method of making a stabilized aerosol drug formulation in which the stability of the formulation is further enhanced. This method comprises combining a solid particulate drug composition with a fluoropolymer in a liquid fluorocarbon aerosol propellant to form a liquid suspension, wherein the fluoropolymer is soluble in the liquid fluorocarbon aerosol propellant, as given above, and further includes the step of cooling the suspension for a time and to a temperature sufficient to adsorb the fluoropolymer to the solid particulate drug composition in the liquid fluorocarbon aerosol propellant.

A third aspect of the present invention is a stabilized aerosol drug formulation produced by the methods described above.

DETAILED DESCRIPTION OF THE INVENTION

Any fluorocarbon aerosol propellant may be employed in carrying out the present invention, including fluorocarbons propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to, $CF_3$—$CHF$—$CF_2H$; $CF_3$—$CH_2$—$CF_2H$; $CF_3$—$CHF$—$CF_3$; $CF_3$—$CH_2$—$CF_3$; $CF_3$—$CHCl$—$CF_2Cl$; $CF_3$—$CHCl$—$CF_3$; cy—$C(CF_2)$—$CHCl$; $CF_3$—$CHCl$—$CH_2Cl$; $CF_3$—$CHF$—$CF_2Cl$; $CF_3$—$CHCl$—$CFHCl$; $CF_3$—$CFCl$—$CFHCl$; $CF_3$—$CF_2$—$CF_2H$; $CF_3$—$CF_2$—$CH_3$; $CF_2H$—$CF_2$—$CFH_2$; $CF_3$—$CF_2$—$CFH_2$; $CF_3$—$CF_2$—$CH_2Cl$; $CF_2H$—$CF_2$13 $CH_3$; $CF_2H$—$CF_2$—$CH_2Cl$; $CF_3$—$CF_2$—$CF_2$—$CH_3$; $CF_3$—$CF_2$—$CF_2$—$CF_2H$; $CF_3$—$CHF$—$CHF$—$CF_3$; $CF_3$—$O$—$CF_3$; $CF_3$—$O$—$CF_2H$; $CF_2H$—$O$—$CF_2H$; $CF_2H$—$O$—$CFH_2$; $CF_3$—$O$—$CH_3$; $CF_3$—$O$—$CF_2$—$CF_2H$; $CF_3$—$O$—$CF_2$—$O$—$CF_2$—; cy—$CF_2$—$CF_2$—$O$—$CF_2$—; cy—$CHF$—$CF_2$—$O$—$CF_2$—; cy—$CH_2$—$CF_2$—$O$—$CF_2$—; cy—$CF_2$—$O$—$CF_2$—$O$—$CF_2$—; $CF_3$—$O$—$CF_2$—$Br$; $CF_2H$—$O$—$CF_2$—$Br$; and mixtures thereof, where "cy" denotes that the propellant is a cyclic compound in which the end terminal covalent bonds of the structures shown are the same so that the end terminal groups are covalently bonded together. Currently preferred are hydrofluoroalkanes such as 1,1,1,2-tetrafluoroethane (propellant 134a) and heptafluoropropane (propellant 227).

The term "fluoropolymer," as used herein, has its conventional meaning in the art. See generally *Fluoropolymers* (L. Wall, Ed. 1972) (Wiley-Interscience Division of John Wiley & Sons); see also *Fluorine-Containing Polymers*, 7 Encyclopedia of Polymer Science and Engineering 256 (H. Mark et al. Eds., 2d Ed. 1985).

The term "soluble," as used herein, is used to indicate that the fluoropolymers are in the same phase as the propellant in the process of the present invention.

Any suitable fluoropolymer may be used in the present invention, including, but not limited to, fluoropolyethers, fluoroacrylates, fluoroolefins, fluorostyrenes, fluoroalkylene oxides (e.g., perfluoropropylene oxide, perfluorocyclohexene oxide), fluorinated vinyl alkyl ether monomers, and the copolymers thereof with suitable comonomers, wherein the comonomers are fluorinated or unfluorinated. The fluoropolymer employed should be pharmaceutically acceptable in that it is essentially free of unduly deleterious side effects when administered as an aerosol to the lungs of a patient in the amounts conventionally employed in a pharmaceutical treatment. Preferred are perfluorinated fluoropolymers (i.e., perfluoropolymers), with the term "perfluorinated," as used herein, meaning that all or essentially all hydrogen atoms on the polymer are replaced with fluorine.

Fluorostyrene polymers and fluorinated polyvinyl alkyl ether which may be employed in the method of the present invention include, but are not limited to, polymers of α-fluorostyrene; β-fluorostyrene; α,β-difluorostyrene; β,β-difluorostyrene; α,β,β-trifluorostyrene; α-trifluoromethylstyrene; 2,4,6-Tris(trifluoromethyl)styrene; 2,3,4,5,6-pentafluorostyrene; 2,3,4,5,6-pentafluoro-α-methylstyrene; and 2,3,4,5,6-pentafluoro-β-methylstyrene.

Tetrafluoroethylene copolymers include, but are not limited to, tetrafluoroethylene-hexafluoropropylene copolymers, tetrafluoroethylene-perfluorovinyl ether copolymers (e.g., copolymers of tetrafluoroethylene with perfluoropropyl vinyl ether), tetrafluoroethylene-ethylene copolymers, and perfluorinated ionomers (e.g., perfluorosulfonate ionomers; perfluorocarboxylate ionomers).

The term "fluoroacrylate polymer," as used herein, refers to polymers of esters of acrylic acid (H₂C=CHCOOH) or methacrylic acid (H₂C=CCH₃COOH), where the esterifying group is a fluorinated group such as perfluoroalkyl. A specific group of polyfluoroacrylate monomers useful in the method of the invention are compounds represented by the formula H₂C=CR¹COO(CH₂)ₙR², wherein n is 1 or 2; R¹ is hydrogen or methyl; and R² is a perfluorinated aliphatic or perfluorinated aromatic group, such as a perfluorinated linear or branched, saturated or unsaturated C1 to C10 alkyl, phenyl, or naphthyl.

Fluoropolyethers are polymeric compounds composed of multiple, sequentially linked, fluorinated aliphatic ether units (e.g., polymers of the formula (RO)ₙ—R wherein the R groups are the same or different and are linear or branched, saturated or unsaturated C1–C4 alkyl; typically linear or branched C1–C4 alkyl, with the number of repeats "n" giving the desired molecular weight); perfluoropolyethers refers to such polymers in which essentially all of the hydrogens have been substituted with fluorine. Two examples of particularly useful perfluoropolyethers are perfluoropolymethyl-isopropyl-ethers such as the polymers of Formula I (marketed under the tradename FOMBLIN ™ by Montefluos SpA, Via Principe Eugenio 1/5, 20155 Milan Italy) and polymers of Formula II (marketed under the tradename AFLUNOX ™).

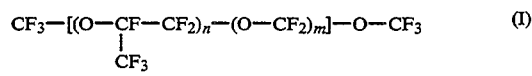

(I)

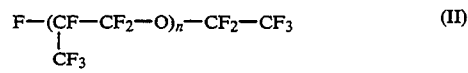

(II)

It will be appreciated by those skilled in this art that the number of units in a polymer, e.g., "n" and "m" in formulas I and II above, are not normally specified, but rather the molecular weight range for the polymer is specified with the number of units being derived therefrom.

Fluoropolymers useful in the present invention typically have molecular weights ranging from about 500 to about 20,000 grams per gram mole, preferably 700 to 10,000 grams per gram mole, more preferably 700 to 6,500 grams per gram mole, and most preferably 700 to 2,000 grams per gram mole. Thus, for example, n and m in formulas I and II above may be integers ranging from two to three to about a hundred.

Fluoropolymers are typically included in the suspensions produced in the present invention in an amount of at least about 0.001% by weight of the total weight of the suspension, preferably in an amount of at least about 0.1% by weight, and more preferably in an amount of at least about 0.5% by weight of the total weight of the suspension. The fluoropolymers are typically included in an amount of not more than about 20% by weight of the total weight of the suspension, preferably in an amount of not more than about 10% by weight, and more preferably in an amount of not more than about 5% by weight of the total weight of the suspension.

Drugs useful in this invention include those drug adaptable to inhalation administration, for example, antiallergic, respiratory (e.g. antiasthmatic and bronchodilating), antibiotic, antiinflammatory, antifungal, analgesic, antiviral, and cardiovascular drugs. Especially useful drugs include the respiratory drugs albuterol, salmeterol and amiloride, fluticasone esters, beclomethasone esters and (−)-4-amino-3,5-dichloro-α-[[[6-(2-pyridinyl)ethoxy]hexyl]amino]methyl]benzenemethanol.

U.S. Pat. No. 3,644,353, incorporated herein by reference, teaches a group of bronchodilating compounds that are particularly useful in the treatment of asthma and other respiratory diseases. The preferred compound taught therein is α1-tert-butylaminomethyl-4-hydroxy-m-xylene-α1, α3-diol, also known in the United States by its generic name, "albuterol" and, in most other countries, "salbutamol."

Salmeterol, chemically named 4-hydroxy-α'-[[[6[(4-phenylbutyl)-oxy]hexyl]amino]methyl]-1,3-benzenedimethanol, disclosed in British Patent Application No. 8,310,477, is a second generation bronchodilator which is longer acting and more potent than albuterol.

The genetic disease cystic fibrosis is characterized by abnormalities that produce excessive pulmonary secretion which can make breathing difficult. U.S. Pat. No. 4,501,729, incorporated herein by reference, discloses the use of the drug amiloride in an aerosol formulation to reduce the excess secretion.

United Kingdom Patent Specification No. 2088877 discloses fluticasone esters. Fluticasone esters are corticosteroids having topical anti-inflammatory action. Corticosteroids may be used in the management of patients whose asthma is inadequately treated by bronchodilators and/or sodium cromoglycate.

A further class of corticosteroids having topical anti-inflammatory action, beclomethasone esters, are described in United Kingdom Patent Specification No. 1 047 519.

(−)-4-Amino-3,5-dichloro-α-[[[6-[2-(2-pyridinyl)ethoxy]hexyl]amino]methyl]benzenemethanol is a bronchodilator.

Where appropriate the drugs may be used in the form of salts (e.g. as alkali metal or amine salts or as acid addition salts) or as esters (e.g. as lower alkyl esters).

For use in the invention, albuterol will preferably be in the form of the sulphate salt or the free base and salmeterol will preferably be in the form of its 1-hydroxy-2-naphthoate salt. The preferred fluticasone ester for use in the invention is fluticasone propionate (FP), and the preferred beclomethasone ester is beclomethasone dipropionate (BDP).

It may be desirable to add other excipients to an aerosol formulation to improve drug delivery, shelf life and patient acceptance. Such optional excipients include, but are not limited to, coloring agents, taste masking agents, buffers, antioxidants and chemical stabilizers.

The drug is typically included in the suspension produced in the present invention in an amount of from 0.001% to 5% by weight, and more typically from 0.005% to 0.5% by weight.

Inhalation drugs, including the pharmaceutically acceptable salt hereof, are typically prepared as small micronized particles by, for example, conventional jet mill micronizing to particles ranging from about 0.1 to about 10.0 microns and preferably from about 0.5 to about 5.0 microns.

A metered-dose inhaler (MDI) containing a stabilized aerosol drug formulation of the present invention is produced by (a) combining a solid particulate drug composition with a fluoropolymer in a liquid fluorocarbon aerosol propellant to form a suspension, as described above, (b) cooling the suspension for a time and to a temperature sufficient to adsorb the fluoropolymer to the solid particulate drug composition in the liquid fluorocarbon, and (c) packaging the suspension in a metered dose inhaler. The cooling step may be carried out before, during, or after the packaging step. We have found the time and temperature of the cooling step to be not particularly critical, so long as it is sufficient to enhance the adsorption of the fluoropolymer to the drug particles. Typically, the suspension is cooled to a temperature of from about 5° C. to about −30° C. for a time of from 5 minutes to 8 hours. The micronized inhalation drug or combination of drugs may optionally be mixed with one or more additional fluorocarbon-soluble surfactants or other excipients. The metered dose inhaler is simply a suitable container capable of withstanding the vapor pressure of the propellant and fitted with a metering valve. The liquid suspension may be forced through the valve into the container, or the suspension may be made by combining the constituents in situ in the container, the container subsequently sealed with a suitable valve to form a completed MDI, and, if necessary, the completed MDI shaken vigorously to form the suspension.

MDI's prepared according to the teachings herein may be used in the same way as currently marketed MDI's which use CFC's or hydrocarbon propellants. For example, in the case of albuterol, the amount of drug, surfactant and propellant can be adjusted to deliver 90 mg per valve actuation (the dose delivered in currently marketed albuterol MDI's).

The present invention is explained in greater detail in the following non-limiting Examples.

EXAMPLE 1–13

Stabilization of Micronized Drug in Hydrofluorocarbon with Perfluoropolyether Micronized drug and polymer were weighed into transparent aerosol vials (such as, but not limited to, those produced by Wheaton Industries, N.J.). A metering valve (such as, but not limited to, those produced by Bespak PLC, England) was crimped onto the vial. Finally, propellant was added to the vial through the valve. Vials were then vigorously shaken for 30 min with a wrist-action shaker. Such formulations could also be produced by adding drug, surfactant and liquified propellant (chilled below it's boiling point) to the container and then sealing the vial by crimping on a metering valve. Sonication could also be used to disperse the drug in the propellant/polymer mixture.

Immediately after shaking, the suspension in the transparent vial was very milky or turbid. If a suspension was left undisturbed, the drug particles would eventually concentrate at the gas/liquid interface (creaming) or at the bottom of the vial (settling) leaving behind a clear propellant solution. By shaking a formulation that had separated, it quickly re-dispersed to a milky suspension. Suspension stability was assessed by monitoring the rate at which the drug particles creamed or settled. In practice, the time required for clear region to develop at the glass/liquid interface or the bottom of vial was measured with a stop-watch. The longer the time required to develop a clear region, the more stable the suspension. Alternatively, several suspensions could be shaken simultaneously and the most stable suspension designated as the last one to separate. A suspension of drug in propellant with no polymer was used as a reference for all other formulations. If the suspension formula with polymer resisted flocculation significantly more the a suspension formula without polymer, it was designated as stabilized.

The examples given in Table 1 are examples of formulations where the perfluoropolyether improved the suspension stability of drugs in hydrofluoroalkanes (HFAs).

Note that suspensions were more stable as the polymer to drug ratio increased.

TABLE 1

| Aerosol Drug Formulations Stabilized with Fluoropolymer | | | |
|---|---|---|---|
| Example No. | Drug/Mass (mg) | Polymer Type | Polymer Mass (g) | 134a Mass (g) |
| 1 | albuterol base/8 | Fomblin YL 06/6 | 0.24 | 7.0 |
| 2 | albuterol base/10 | Fomblin YL 25/5 | 0.25 | 7.0 |
| 3 | albuterol base/10 | Fomblin YH 18/8 | 0.10 | 7.0 |
| 4 | albuterol | Fomblin YH | 0.25 | 7.0 |

TABLE 1-continued

Aerosol Drug Formulations Stabilized with Fluoropolymer

| Example No. | Drug/Mass (mg) | Polymer Type | Polymer Mass (g) | 134a Mass (g) |
|---|---|---|---|---|
| | base/8 | 18/8 | | |
| 5 | albuterol base/10 | Fomblin YH 18/8 | 0.25 | 7.0 |
| 6 | albuterol base/8 | Fomblin YH 18/8 | 0.32 | 7.0 |
| 7 | salmeterol hydroxynapthoate/3 | Fomblin YH 18/8 | 0.25 | 7.0 |
| 8 | salmeterol hydroxynapthoate/10 | Fomblin YH 18/8 | 0.25 | 7.0 |
| 9 | BDP/9 | Fomblin YH 18/8 | 0.25 | 7.0 |
| 10 | amiloride/10 | Fomblin YH 18/8 | 0.25 | 7.0 |
| 11 | FP/26 | Fomblin YH 18/8 | 0.25 | 18.0 |
| 12 | FP/26 | Fomblin YH 18/8 | 0.5 | 18.0 |
| 13 | albuterol base/25 | Aflunox 6008 | 0.5 | 18.0 |

EXAMPLES 14–25

Effect of Chilling on Stabilization of Micronized Drug in Hydrofluorocarbon

These examples were carried out in essentially the same manner as Examples 1–13 above, except that the effect of introducing a chilling step at various points during the process was Examined. Note that Albuterol base is less dense than the hydrofluorocarbon propellant 134a. Therefore, albuterol base particles in 134a will eventually rise to the gas/liquid interface (cream). Perfluoropolyethers, on the other hand, have densities of approximately 1.7 to 1.9 grams/cubic centimeter.

As shown in Table 2 below, as storage temperature decreased, the albuterol base formulation with the perfluoropolyether settled rather than creamed. This means that the drug particles became denser than the propellant. As temperature decreases, HFA's density increases also. Therefore, the settling observed in perfluoropolyether formulations means that the polymer must adsorb more strongly onto the drug particle at lower temperatures. Thus, by lowering the temperature of the formulation, the adsorption of perfluoropolyethers on drug particle surfaces is increased. This unexpected result is very beneficial to micronized drug formulations in HFAs since polymer adsorption at interfaces (e.g., drug surface/HFA) aids in stabilizing suspensions.

In Table 2, data are given for formulations where suspension stability was improved by storing the inhalers at 5° C. for eight hours. These inhalers were manufactured at room temperature, chilled, and then returned to room temperature.

TABLE 2

Effect of Storage Temperature on Aerosol Drug Formulations Stabilized with Fluoropolymers

| Example Number | Mass of Albuterol (grams) | Mass of Fomblin (grams) | Mass of Propellant 134a-grams | Storage Temperature | Settling or Creaming |
|---|---|---|---|---|---|
| 14 | 24 | .5 HC25 | 18 | Room Temp. | Creaming |
| 15 | 28 | 0 | 7.1 | Room Temp. | Creaming |
| 16 | 24 | .5 HC25 | 18 | 0° C. | Settling |
| 17 | 28 | 0 | 7.1 | 0° C. | Creaming |
| 18 | 24 | .5 HC25 | 18 | −30° C. | Settling |
| 19 | 28 | 0 | .1 | −30° C. | Creaming |

The data set forth in Table 3 are examples of formulations in which the suspension stability was improved by storing the inhalers at 5° C. for eight hours. These inhalers were manufactured at room temperature, chilled, and then returned to room temperature.

TABLE 3

Effect of Storage Temperature on Aerosol Drug Formulations Stabilized with Fluoropolymers

| Example Number | Drug/Mass (mg) | Polymer Type | Polymer Mass (g) | 134a Mass (g) |
|---|---|---|---|---|
| 20 | albuterol base/25 | Fomblin HCO4 Aflunox 6008 | 0.15 .1 | 18.0 |
| 21 | albuterol base/25 | Aflunox 1106 | 0.5 | 18.0 |
| 22 | albuterol base/24 | Fomblin HC25 | 0.5 | 18.0 |
| 23 | albuterol base/24 | Fomblin HC25 | 0.1 | 18.0 |

The data set forth in Table 4 are examples in which a chilling process, which was carried out in a methanol/dry ice bath for 5–10 minutes, improved suspension stability:

TABLE 4

Effect of Chilling on Fluoropolymer Stabilized Aerosol Drug Formulations

| Example Number | Drug/Mass (mg) | Polymer Type | Polymer Mass (g) | 134a Mass (g) |
|---|---|---|---|---|
| 24 | albuterol base/26 | Fomblin HCO4 | 0.05 | 18.25 |
| 25 | albuterol base/26 | Fomblin YN 40/11 | 0.15 | 18.45 |

From Table 2 through 4, it will be seen that the temperature range for the operation of the method of the present invention is quite wide, and can be embodied in a variety of different processes.

The foregoing examples are illustrative of the present invention, and are not to be construed as limiting thereof. The invention is defined by the following claims, with equivalents of the claims to be included therein.

That which is claimed is:

1. A method of adsorbing a solid particulate drug to a fluoropolymer useful for making a stabilized aerosol drug formulation, comprising:

combining a solid particulate drug with a fluoropolymer in an organic liquid fluorocarbon aerosol propellant to form a liquid suspension, wherein said fluoropolymer is soluble in said liquid fluorocarbon aerosol propellant, wherein said fluoropolymer is included in said suspension in an amount of from 0.001% to 20% by weight, and wherein said drug is included in said suspension in an amount of from 0.001% to 5% by weight; and cooling said suspension for a time and to a temperature sufficient to adsorb said fluoropolymer to said solid particulate drug in said liquid fluorocarbon aerosol propellant, wherein said fluoropolymer is adsorbed to said drug so that said formulation is stabilized.

2. The method of claim 1, wherein said fluoropolymer is a fluoropolyether.

3. The method of claim 1, wherein said fluoropolymer has a molecular weight of from 500 to 25,000 grams per gram mole.

4. The method of claim 1, wherein said fluoropolymer is included in said suspension in an amount of from 0.1% to 10% by weight.

5. The method of claim 1, wherein said drug is included in said suspension in an amount of from 0.005% to 0.5% by weight.

6. The method of claim 1, wherein said propellant is selected from the group consisting of 1,1,1,2-tetrafluoroethane and heptafluoropropane.

7. The method of claim 1, wherein said solid particulate drug is a micronized drug.

8. The method of claim 1 wherein said drug is selected from the group consisting of albuterol, salmeterol, amiloride, fluticasone esters, beclomethasone esters and (−)-4-amino-3,5-dichloro-α-[[[6-(2-pyridinyl)ethoxy]hexyl]amino]methyl benzenemethanol.

9. The method of claim 1 wherein said drug is albuterol.

10. A method of adsorbing a solid particulate drug to a fluoropolymer useful for making a metered-dose inhaler containing a stabilized aerosol drug formulation, comprising:

combining a solid particulate drug with a fluoropolymer in an organic liquid fluorocarbon aerosol propellant to form a suspension, wherein said fluoropolymer is soluble in said liquid fluorocarbon aerosol propellant, wherein said fluoropolymer is included in said suspension in an amount of from 0.001% to 20% by weight, and wherein said drug is included in said suspension in an amount of from 0.001% to 5% by weight;

cooling said suspension for a time and to a temperature sufficient to adsorb said fluoropolymer to said solid particulate drug in said liquid fluorocarbon; and packaging said suspension in a metered dose inhaler;

wherein said cooling step is carried out before, after, or concurrently with said packaging step, wherein said fluoropolymer is adsorbed to said drug so that said formulation is stabilized.

11. A method according to claim 10, wherein said cooling step is carried out before said packaging step.

12. A method according to claim 10, wherein said cooling step is carried out after said packaging step.

13. A method according to claim 10, wherein said cooling step is carried out concurrently with said packaging step.

14. The method of claim 11, wherein said fluoropolymer is a fluoropolyether.

15. The method of claim 10, wherein said fluoropolymer has a molecular weight of from 500 to 25,000 grams per gram mole.

16. The method of claim 10, wherein said fluoropolymer is included in said suspension in an amount of from 0.1% to 10% by weight.

17. The method of claim 10, wherein said drug is included in said suspension in an amount of from 0.005% to 0.5% by weight.

18. The method of claim 10, wherein said propellant is selected from the group consisting of 1,1,1,2-tetrafluoroethane, heptafluoropropane, and mixtures thereof.

19. The method of claim 10, wherein said solid particulate drug is a micronized drug.

20. The method of claim 11 wherein said drug is selected from the group consisting of albuterol, salmeterol, amiloride, fluticasone esters, beclomethasone esters and (−)-4-amino-3,5-dichloro-α-[[[6-(2-pyridinyl)ethoxy]hexyl]amino]methyl benzenemethanol.

21. The method of claim 10 wherein said drug is albuterol.

* * * * *

UNITED STATES PATENT AND TRADEMARK OFFICE
CERTIFICATE OF CORRECTION

PATENT NO. : 5,376,359
DATED : December 27, 1994
INVENTOR(S) : Keith A. Johnson

It is certified that error appears in the above-identified patent and that said Letters Patent is hereby corrected as shown below:

Column 2, line 51 & 52, please correct last " $(CF_2)$ " to read -- $(CF_2)_3$ --.

Column 2, line 56, please delete " 13 " and correct with a dash -- - --.

Column 2, line 60, please correct last " $CF_2$ " in the line to read -- $CF_3$ --.

Column 10, Claim 14, line 19, please correct " claim 11 " to read -- claim 10 --.

Column 10, Claim 20, line 36, please correct " claim 11 " to read -- claim 10 --.

Signed and Sealed this

Second Day of May, 1995

Attest:

BRUCE LEHMAN

*Attesting Officer*    *Commissioner of Patents and Trademarks*